(12) United States Patent
Carlson et al.

(10) Patent No.: US 10,961,163 B2
(45) Date of Patent: Mar. 30, 2021

(54) COMPOSITIONS AND METHODS USEFUL FOR ENHANCING THE MICROBIAL CONVERSION OF NITRATE INTO AMMONIUM

(71) Applicant: The Regents of the University of California, Oakland, CA (US)

(72) Inventors: Hans Karl Carlson, Albany, CA (US); Adam M. Deutschbauer, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 128 days.

(21) Appl. No.: 15/687,380

(22) Filed: Aug. 25, 2017

(65) Prior Publication Data

US 2018/0057417 A1    Mar. 1, 2018

Related U.S. Application Data

(60) Provisional application No. 62/379,710, filed on Aug. 25, 2016.

(51) Int. Cl.
| | | |
|---|---|---|
| C05C 11/00 | (2006.01) | |
| C05C 5/00 | (2006.01) | |
| C05C 1/00 | (2006.01) | |
| C05C 3/00 | (2006.01) | |
| C05F 11/00 | (2006.01) | |
| A01N 31/02 | (2006.01) | |
| C12Q 1/02 | (2006.01) | |

(52) U.S. Cl.
CPC .............. *C05C 11/00* (2013.01); *A01N 31/02* (2013.01); *C05C 1/00* (2013.01); *C05C 3/00* (2013.01); *C05C 5/00* (2013.01); *C05F 11/00* (2013.01); *C12Q 1/025* (2013.01)

(58) Field of Classification Search
None
See application file for complete search history.

(56) References Cited

U.S. PATENT DOCUMENTS

| | | | | |
|---|---|---|---|---|
| 2005/0197252 A1* | 9/2005 | Yamashita | ............. | A01N 25/32 504/103 |
| 2011/0252847 A1* | 10/2011 | Nasholm | ................ | A01N 37/44 71/11 |
| 2014/0271535 A1* | 9/2014 | Yamashita | ............... | C05G 3/00 424/84 |
| 2015/0239788 A1* | 8/2015 | Yamashita | ............. | C05F 11/08 504/101 |

* cited by examiner

*Primary Examiner* — Wayne A Langel
(74) *Attorney, Agent, or Firm* — Robin C. Chiang; Lawrence Berkeley National Laboratory

(57) ABSTRACT

The present invention provides for methods of and compositions for enhancing microbial conversion of nitrate into ammonium. The methods and compositions alter the end products of microbial nitrate reduction to improve agricultural efficiency and lead to more sustainable and economically profitable agricultural practices.

7 Claims, 2 Drawing Sheets

COMPOSITIONS AND METHODS USEFUL FOR ENHANCING THE MICROBIAL CONVERSION OF NITRATE INTO AMMONIUM

CROSS-REFERENCE TO RELATED APPLICATIONS

The application claims priority to U.S. Provisional Patent Application Ser. No. 62/379,710, filed Aug. 25, 2016, which is herein incorporated by reference in its entirety.

STATEMENT OF GOVERNMENTAL SUPPORT

This invention was made during work supported by U.S. Department of Energy under Contract No. DE-AC02-05CH11231. The government has certain rights in this invention.

BACKGROUND OF THE INVENTION

Field of the Invention

The present invention relates to methods and compositions for enhancing nitrogen fertilizer efficiency including using selective carbon sources and inorganic oxyganions that influence the endproducts of microbial nitrate reduction.

Related Art

Much nitrogen applied to agricultural soils in the form of fertilizer is converted, through microbial nitrification, to nitrate. This nitrate is then reduced by microorganisms either to dinitrogen ($N_2$) by nitrate reducers (NR) or to ammonium ($NH_4^+$). Through these microbially mediated processes much fertilizer nitrogen is lost to the atmosphere as gaseous endproducts and intermediates. At present, fertilizer application is only about 17% efficient. Altering the end products of microbial nitrate reduction could improve agricultural efficiency and lead to more sustainable and economically profitable agricultural practices.

BRIEF SUMMARY OF THE INVENTION

The present invention provides for methods of and compositions for enhancing microbial conversion of nitrate into ammonium. The present invention describes a high-throughput assay for the prediction of the influence of carbon sources and geochemically relevant inorganic compounds on the extent of ammonium production in microbial ecosystems. These predictions can be used to predict nitrate efficacy based on analysis of carbon source and metal profiles and design strategies to increase the efficiency of crop fertilization. Thus, in some embodiments, the present invention provides for compositions and methods for enhancing nitrogen fertilizer efficiency.

BRIEF SUMMARY OF THE INVENTION

Figure 1:
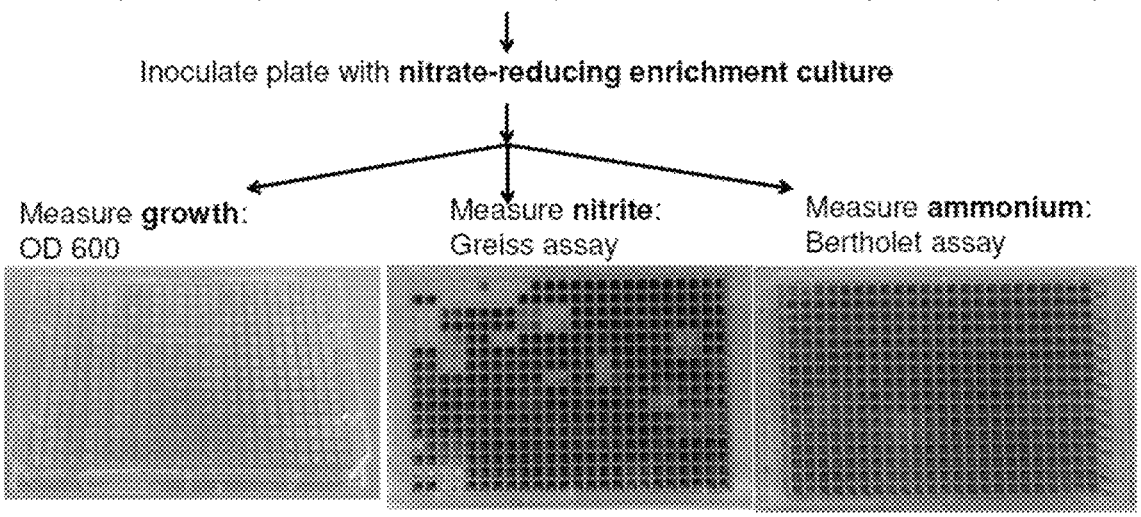
FIG. 1 presents an assay format. Growth is measured in microbial enrichment cultures by OD 600, nitrite is measured by the Greiss assay, and ammonium is measured using a colorimetric assay (Bertholet assay). By cultivating a microbial enrichment on individual carbon sources the ammonium production potential normalized by the total growth, the $NH_4^+/OD$ ratio, can be determined (FIG. 2, Table 1). The higher the ammonium/OD ratio the greater the propensity of a given carbon source to drive microbial nitrite production. By cultivating the microbial enrichment with a complex carbon source (yeast extract), in the presence of serial dilutions of inorganic compounds we can determine the inhibitory potency ($IC_{50}$) against growth and ammonium production. The ratio of the ammonium $IC_{50}$ and growth $IC_{50}$ values ($NH_4^+$ $IC_{50}$/growth $IC_{50}$) can be determined (FIG. 3, Table 2). The higher $NH_4^+$ $IC_{50}$/growth $IC_{50}$ ratio the more a compound favors ammonium production, and the lower the $NH_4^+$ $IC_{50}$/growth $IC_{50}$ ratio the more a compound disfavors ammonium production. Relative nitrite or ammonium production can be quantified based on $NO_2^-/OD$ or $NH_4^+/OD$, or by comparing inhibitory potencies of compounds based on $IC_{50} NO_2^-/IC_{50}$ OD or $IC_{50} NH_4^+/IC_{50}$ OD.
Figure 2:
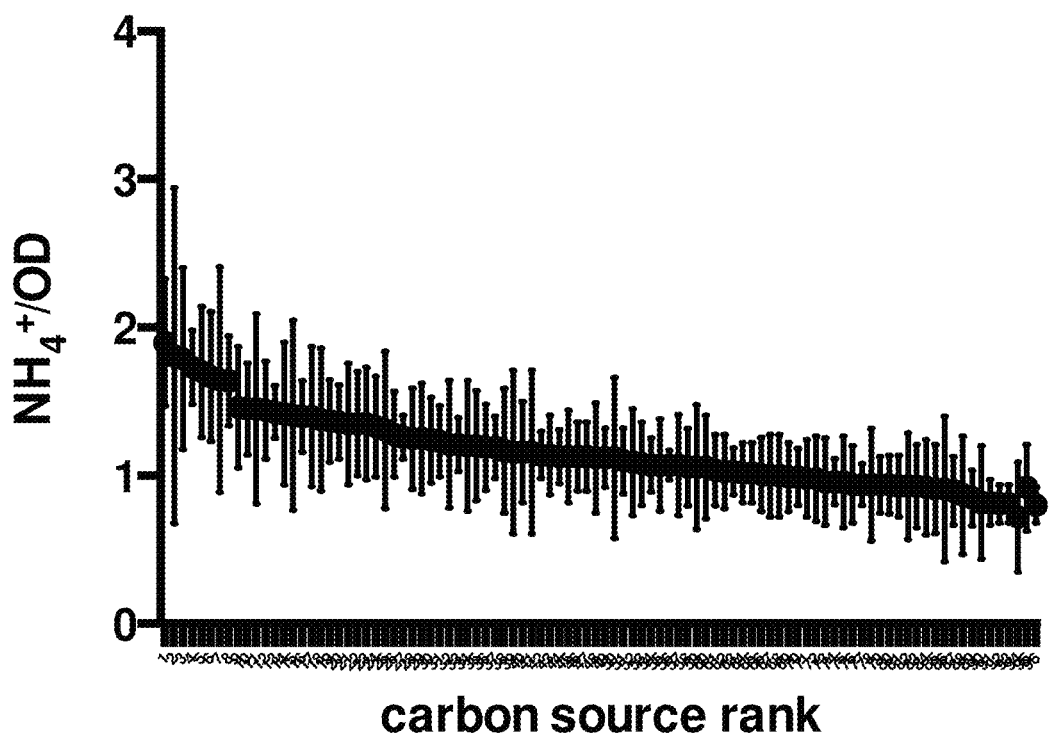
FIG. 2. $NH_4^+/OD$ ratios for carbon sources.
Figure 3:
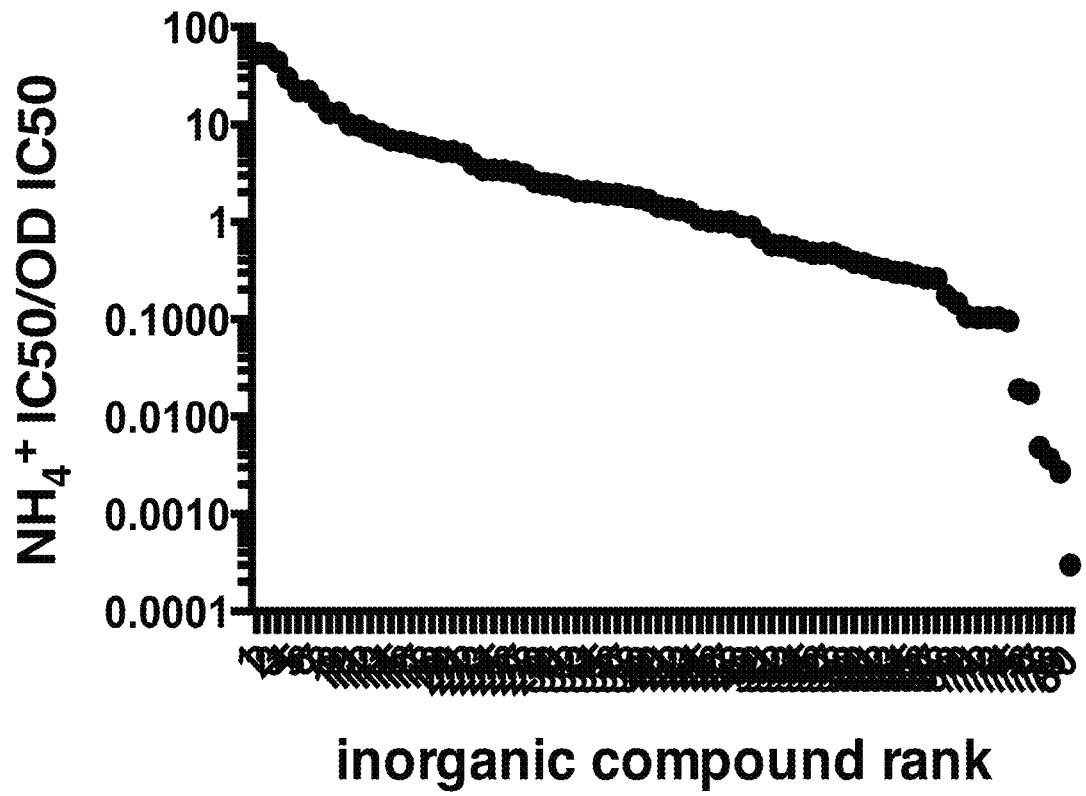
FIG. 3. $NH_4^+$ $IC_{50}/OD$ $IC_{50}$ ratios for inorganic compounds.
Figure 4:
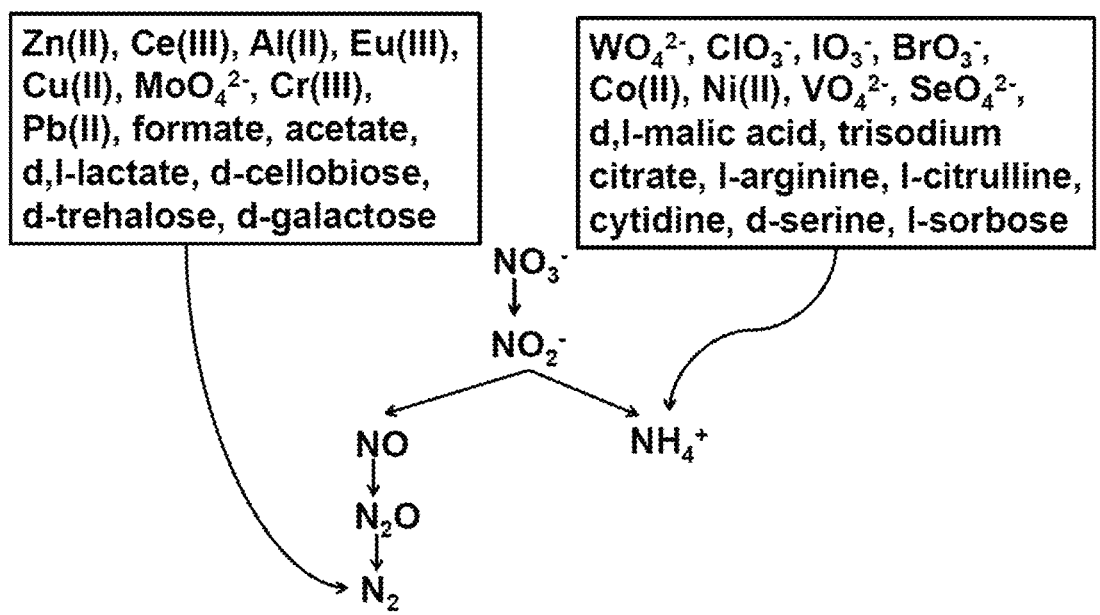
FIG. 4. Based on the results, the candidate determinants of $NH_4^+$ vs. $N_2$ are shown.

Specific carbon sources can alter the end products of nitrate reduction, and certain metals and inorganic compounds can alter the end products of nitrate reduction. Thus, in some embodiments, we describe compositions and methods for enhancing nitrogen fertilizer efficiency.

The present invention provides for a method of enhancing microbial conversion of nitrate into ammonium comprising: administering to a soil or substrate a first composition and/or a second composition of the present invention. In some embodiments, the soil or substrate has a plant or plants planted, or a seed or seeds sowed, in the soil or substrate. The planting or sowing can be before, during, or after the administering step. In some embodiments, the method further comprises introducing of a fertilizer and/or nitrate to the soil or substrate. The planting or sowing can be before, during, or after the administering step and/or the planting or sowing step. In some embodiments, the administering step is preceded by a diluting a concentrate or anhydrous first and/or second composition. The first composition and the second composition, or a diluted first and/or second composition, comprises the organic compound(s) and/or the inorganic compound(s) in concentrations that are not harmful to the plant or plants, or the seed or seeds. In some embodiments, the soil or substrate is suspected or known to be deficient or poor in nitrogen containing compounds necessary for plant growth.

The present invention provides for the first composition and/or the second composition. In some embodiments, the first composition and/or the second composition are simple or defined solutions.

The first composition comprises one or more, two or more, three or more, four or more, five or more, six of more, seven or more, eight or more, nine or more, ten or more, 15 or more, 20 or more, 25 or more, 30 or more, 35 or more, 40 or more, 45 or more, 50 or more, or all, of the following carbon compounds: L-Sorbose, D-Serine, L-Arginine, Trisodium citrate dehydrate, L-Arabinose, L-Methionine, Citric Acid, Cytidine, L-Citrulline, L-Alanine, Carnitine Hydrochloride, Inosine, L-Malic acid disodium salt monohydrate, D-Fructose, D,L-Malic Acid, L-Phenylalanine, Itaconic Acid, Glucuronamide, Cytosine, D-Ribose, Sodium L-Lactate, L-Threonine, D-Salicin, D-Glucose, 4-Hydroxybenzoic Acid, L-Glutamine, a-Ketoglutaric acid disodium salt hydrate, m-Inositol, Adenosine, L-Aspartic Acid, L-Tryptophan, Sodium octanoate, D-Arabinose, Putrescine Dihydrochloride, L-Serine, Glycerol, D-Gluconic Acid sodium salt, Gly-DL-Asp, L-Asparagine, D-Glucosamine Hydrochloride, Sodium D-Lactate, D-Tagatose, D-Cellobiose, L-Isoleucine, Xylitol, Potassium oxalate monohydrate, Thymine, Gly-Glu, Parabanic Acid, 5-Keto-D-Gluconic Acid potassium salt, L-Histidine, L-Rhamnose monohydrate, D-Alanine, Sucrose, N-Acetyl-D-Glucosamine, a-Cyclodextrin, L-Leucine, L-Fucose, D-Xylose, Thymidine, Sodium butyrate, Sodium succinate dibasic hexahydrate, D-Raffinose pentahydrate, D-Glucuronic Acid, L-Lysine, and Glycolic Acid.

The first composition, or a second composition, comprises one or more, two or more, three or more, four or more, five or more, six of more, seven or more, eight or more, nine or more, ten or more, 15 or more, 20 or more, 25 or more, 30 or more, 35 or more, 40 or more, 45 or more, 50 or more, or all, of the following inorganic compounds: Sodium bromate, Nickel (II) chloride hexahydrate, Ethylenediamine-N, N'-disuccinic acid, Cesium chloride, Cobalt chloride hexahydrate, Sodium Chloride, sodium iodate, Sodium metavanadate, Sodium 2-mercaptoethanesulfonate, Sodium selenite, Sodium hypophosphite monohydrate, Hans 100× vitamins, Sodium periodate, Magnesium chloride hexahydrate, Sodium molybdate, 9,10-Anthraquinone-2,7-disulphonic acid (AQDS), Sodium cholate hydrate, Potassium chromate, Sodium 2-bromoethanesulfonate, Sodium perchlorate monohydrate, Gallic Acid, Sodium m-arsenite, Sodium nitrate, Lithium chloride, Strontium chloride, Sodium arsenate dibasic heptahydrate, Bile salts, Sodium silicate, sodium sulfite, Sodium antimonite, Gjerstad humics, Ammonium sulfite monohydrate, Vanillyl Alcohol, dimethyl sulfone, silver sulfate, Sodium Chlorate, Sodium tungstate dehydrate, potassium tellurate, sodium fluoride, rubidium chloride, 4-Hydroxyacetophenone, Sodium phosphite dibasic pentahydrate, Sodium Chlorite, Sodium Fluorophosphate, Ammonium chloride, and Gallium (III) chloride.

In some embodiments, the composition comprises one or more, two or more, three or more, four or more, five or more, six of more, seven or more, eight or more, nine or more, ten or more, or all, of the following: $WO_4^{2-}$, $ClO_3^-$, $IO_3^-$, $BrO_3^-$, Co (III), Ni (II), $VO_4^{2-}$, $SeO_4^{2-}$, D, L-malic acid, L-arginine, L-citrulline, cytidine, D-serine, and L-sorbose.

In some embodiments, the first composition and/or second composition lacks any carbon compound when tested using the method described for FIG. 1 herein produces an ammonium/OD ratio of equal to 1.00 or less, equal to 0.95 or less, equal to 0.90 or less, equal to 0.85 or less, or equal to 0.80 or less. In some embodiments, the composition lacks one or more, two or more, three or more, four or more, five or more, six of more, seven or more, eight or more, nine or more, ten or more, 15 or more, 20 or more, 25 or more, or all, of the carbon compounds listed in Table 1 which have a corresponding ammonium/OD ratio of equal to 1.00 or less, equal to 0.95 or less, equal to 0.90 or less, equal to 0.85 or less, or equal to 0.80 or less.

In some embodiments, the first composition and/or second composition lacks any inorganic compound when tested using the method described for FIG. 1 herein produces an $NH_4^+$ $IC_{50}$/growth $IC_{50}$ ratio of equal to 1.00 or less, equal to 0.90 or less, equal to 0.80 or less, equal to 0.70 or less, equal to 0.60 or less, equal to 0.50 or less, equal to 0.40 or less, equal to 0.30 or less, equal to 0.20 or less, or equal to 0.10 or less. In some embodiments, the first composition and/or second composition lacks one or more, two or more, three or more, four or more, five or more, six of more, seven or more, eight or more, nine or more, ten or more, 15 or more, 20 or more, 25 or more, 30 or more, or all, of the inorganic compounds listed in Table 2 which have a corresponding $NH_4^+$ $IC_{50}$/growth $IC_{50}$ ratio of equal to 1.00 or less, equal to 0.90 or less, equal to 0.80 or less, equal to 0.70 or less, equal to 0.60 or less, equal to 0.50 or less, equal to 0.40 or less, equal to 0.30 or less, equal to 0.20 or less, or equal to 0.10 or less.

In some embodiments, the first composition and/or second composition lacks one or more, two or more, three or more, four or more, five or more, six of more, seven or more, eight or more, nine or more, ten or more, or all, of the following: Zn (II), Ce (III), Al (II), Eu (III), Cu (II), $MoO_4^{2-}$, Cr (III), Pb (II), formate, acetate, D,L-lactate, D-cellobiose, D-trehalose, and D-galactose.

In some embodiments, the first composition and/or the second composition is an aqueous solution, or in an anhydrous state, such as crystals and/or powder. In some embodiments, when the first composition and/or the second composition is an aqueous solution, the carbon compounds and/or the inorganic compounds are in a concentrated form, such as they are an 10×, 100× or 1000× concentration, which needs to be diluted with water, or any other suitable solvent, prior to administering to fertilizer, nitrate, soil, or substrate.

In some embodiments, a high-throughput assay for the prediction of the influence of carbon sources and geochemically relevant inorganic compounds on the extent of ammonium production in microbial ecosystems. Various carbon sources, such as sugars, amino acids and nucleotides, are predicted to influence ammonium production differently. Inorganic compounds can greatly influence the capacity for nitrate reduction and can alter end-products.

Predicting nitrate efficacy based on analysis of carbon source and metal profiles of the system provide for methods and design strategies to increase the efficiency of crop fertilization. By altering and supplementing the profile of a system through addition of carbon source and inorganic compounds, in some embodiments, compositions are developed for increasing nitrogen efficiency, increased ammonium production, the reduction of nitrates, or altering nitrate reaction end products.

In some embodiments, the compounds shown in Tables 1 and 2 are added to a system, e.g., through a fertilizer and compost, to increase nitrogen efficiency. In some embodiments, the top 1, 2, 3, 4, 5, 6, 7, 8, 9, 10, 20, 30, or 40, or any number within a range of any two preceding numbers, compounds in Table 1 and/or Table 2 are used as a supplement or augment to nitrogen fertilizers to improve their efficacy as these compounds can be used to drive or increase ammonium production.

The present invention also provides for a method of identifying organic compounds or inorganic compounds that enhance or inhibit microbial conversion of nitrate into ammonium, comprising the steps described herein.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

TABLE 1

Ammonium/OD ratios for carbon sources in rank order. Highest Ammonium/OD ratio indicates most ammonium production enhancing carbon source. Ammonium/OD ratio are the average of 8 independent cultures amended with varying concentrations of the carbon source.

| Carbon source | Ammonium/OD ratio | standard deviation |
| --- | --- | --- |
| L-Sorbose | 1.90 | 0.43 |
| D-Serine | 1.81 | 1.13 |
| L-Arginine | 1.79 | 0.61 |
| Trisodium citrate dihydrate | 1.73 | 0.25 |
| L-Arabinose | 1.70 | 0.44 |
| L-Methionine | 1.67 | 0.44 |
| Citric Acid | 1.65 | 0.76 |
| Cytidine | 1.64 | 0.30 |
| L-Citrulline | 1.46 | 0.41 |
| L-Alanine | 1.45 | 0.31 |
| Carnitine Hydrochloride | 1.45 | 0.64 |
| Inosine | 1.44 | 0.33 |
| L-Malic acid disodium salt monohydrate | 1.43 | 0.18 |
| D-Fructose | 1.42 | 0.48 |
| D,L-Malic Acid | 1.41 | 0.64 |
| L-Phenylalanine | 1.40 | 0.24 |
| Itaconic Acid | 1.40 | 0.47 |
| Glucuronamide | 1.38 | 0.48 |
| Cytosine | 1.37 | 0.28 |
| D-Ribose | 1.36 | 0.25 |
| Sodium L-Lactate | 1.35 | 0.41 |
| L-Threonine | 1.35 | 0.35 |
| D-Salicin | 1.35 | 0.38 |
| D-Glucose | 1.33 | 0.34 |
| 4-Hydroxybenzoic Acid | 1.31 | 0.53 |
| L-Glutamine | 1.28 | 0.29 |
| a-Ketoglutaric acid disodium salt hydrate | 1.26 | 0.15 |
| m-Inositol | 1.25 | 0.34 |
| Adenosine | 1.25 | 0.37 |
| L-Aspartic Acid | 1.24 | 0.29 |
| L-Tryptophan | 1.23 | 0.24 |
| Sodium octanoate | 1.21 | 0.43 |
| D-Arabinose | 1.21 | 0.18 |
| Putrescine Dihydrochloride | 1.20 | 0.44 |
| L-Serine | 1.20 | 0.37 |
| Glycerol | 1.19 | 0.29 |
| D-Gluconic Acid sodium salt | 1.19 | 0.21 |
| Gly-DL-Asp | 1.17 | 0.42 |
| L-Asparagine | 1.16 | 0.55 |
| D-Glucosamine Hydrochloride | 1.16 | 0.34 |
| Sodium D-Lactate | 1.16 | 0.55 |
| D-Tagatose | 1.14 | 0.16 |
| D-Cellobiose | 1.14 | 0.27 |
| L-Isoleucine | 1.13 | 0.18 |
| Xylitol | 1.13 | 0.31 |
| Potassium oxalate monohydrate | 1.13 | 0.23 |
| Thymine | 1.13 | 0.23 |
| Gly-Glu | 1.12 | 0.37 |
| Parabanic Acid | 1.12 | 0.20 |
| 5-Keto-D-Gluconic Acid potassium salt | 1.12 | 0.54 |
| L-Histidine | 1.10 | 0.22 |
| L-Rhamnose monohydrate | 1.09 | 0.36 |
| D-Alanine | 1.08 | 0.28 |
| Sucrose | 1.07 | 0.18 |
| N-Acetyl-D-Glucosamine | 1.07 | 0.31 |
| a-Cyclodextrin | 1.07 | 0.10 |
| L-Leucine | 1.07 | 0.34 |
| L-Fucose | 1.06 | 0.26 |
| D-Xylose | 1.06 | 0.42 |
| Thymidine | 1.06 | 0.35 |
| Sodium butyrate | 1.04 | 0.24 |
| Sodium succinate dibasic hexahydrate | 1.03 | 0.25 |
| D-Raffinose pentahydrate | 1.03 | 0.16 |
| D-Glucuronic Acid | 1.02 | 0.20 |
| L-Lysine | 1.02 | 0.20 |
| Glycolic Acid | 1.01 | 0.25 |
| 2-Deoxy-D-Ribose | 1.00 | 0.28 |
| L-Cysteine hydrochloride monohydrate | 1.00 | 0.28 |
| D-Glucose-6-Phosphate sodium salt | 0.99 | 0.23 |
| Beta-Lactose | 0.99 | 0.19 |
| Potassium acetate | 0.98 | 0.26 |
| L-Glutamic acid monopotassium salt monohydrate | 0.98 | 0.29 |
| Sodium pyruvate | 0.96 | 0.29 |
| Uridine | 0.96 | 0.15 |
| D-Mannose | 0.96 | 0.31 |
| Sodium propionate | 0.94 | 0.26 |
| Glycine | 0.94 | 0.14 |
| L-Valine | 0.94 | 0.38 |
| D-Maltose monohydrate | 0.94 | 0.19 |
| L-Proline | 0.94 | 0.20 |
| Adenine hydrochloride hydrate | 0.93 | 0.21 |
| casamino acids | 0.93 | 0.36 |
| D-Galactose | 0.93 | 0.28 |
| D-Galacturonic Acid monohydrate | 0.92 | 0.32 |
| Ethanol | 0.91 | 0.30 |
| Sodium D,L-Lactate | 0.91 | 0.49 |
| D-Mannitol | 0.90 | 0.23 |
| L-tyrosine disodium salt | 0.87 | 0.40 |
| Gelatin | 0.85 | 0.19 |
| D-Sorbitol | 0.82 | 0.38 |
| D-Trehalose dihydrate | 0.82 | 0.15 |
| Sodium Fumarate dibasic | 0.81 | 0.13 |
| Tween 20 | 0.81 | 0.13 |
| Sodium Formate | 0.72 | 0.37 |

TABLE 2

$NH_4^+$ $IC_{50}$/growth $IC_{50}$ ratios for inorganic compound sources

| Inorganic compound | $NH_4^+$ $IC_{50}$/growth $IC_{50}$ ratio |
| --- | --- |
| Sodium bromate | 53.7262 |
| Nickel (II) chloride hexahydrate | 53.6273 |
| Ethylenediamine-N,N'-disuccinic acid | 44.3418 |
| Cesium chloride | 30.1708 |
| Cobalt chloride hexahydrate | 22.1846 |
| Sodium Chloride | 21.9487 |
| sodium iodate | 17.3080 |
| Sodium metavanadate | 13.0898 |
| Sodium 2-mercaptoethanesulfonate | 13.0401 |
| Sodium selenate | 10.0581 |
| Sodium hypophosphite monohydrate | 9.6768 |
| Hans 100x vitamins | 8.4473 |
| Sodium periodate | 7.8824 |
| Magnesium chloride hexahydrate | 6.9447 |
| Sodium molybdate | 6.7259 |
| AQDS | 6.4905 |
| Sodium cholate hydrate | 5.9537 |
| Potassium chromate | 5.7062 |
| Sodium 2-bromoethanesulfonate | 5.3024 |
| Sodium perchlorate monohydrate | 5.2779 |
| Gallic Acid | 4.9374 |
| Sodium m-arsenite | 3.9664 |
| Sodium nitrate | 3.4080 |
| Lithium chloride | 3.4054 |
| Strontium chloride | 3.3568 |
| Sodium arsenate dibasic heptahydrate | 3.2618 |
| Bile salts | 3.0880 |
| Sodium silicate | 2.5921 |
| sodium sulfite | 2.4699 |
| Sodium antimonate | 2.4203 |
| Gjerstad humics | 2.3114 |
| Ammonium sulfite monohydrate | 2.0739 |
| Vanillyl Alcohol | 2.0632 |
| dimethyl sulfone | 2.0187 |
| silver sulfate | 1.9192 |

TABLE 2-continued

NH$_4^+$ IC$_{50}$/growth IC$_{50}$ ratios for inorganic compound sources

| Inorganic compound | NH$_4^+$ IC$_{50}$/growth IC$_{50}$ ratio |
|---|---|
| Sodium Chlorate | 1.9090 |
| Sodium tungstate dihydrate | 1.8289 |
| potassium tellurate | 1.7673 |
| sodium fluoride | 1.6628 |
| rubidium chloride | 1.4483 |
| 4-Hydroxyacetophenone | 1.3700 |
| Sodium phosphite dibasic pentahydrate | 1.3336 |
| Sodium Chlorite | 1.2683 |
| Sodium Fluorophosphate | 1.0647 |
| Ammonium chloride | 1.0157 |
| Gallium(III)chloride | 1.0037 |
| Sodium sulfate | 1.0000 |
| Sodium thiophosphate tribasic hydrate | 0.8963 |
| Sodium cyanide | 0.8871 |
| Sodium pyrophosphate dibasic | 0.6988 |
| sodium bromide | 0.5766 |
| Sodium thiosulfate pentahydrate | 0.5741 |
| Hans 1000x minerals | 0.5533 |
| Sodium carbonate | 0.5039 |
| Potassium Chloride | 0.4776 |
| Nitrilotriacetic acid | 0.4756 |
| Palladium(II) chloride | 0.4739 |
| Sodium methanesulfonate | 0.4289 |
| Hydroxylamine hydrochloride | 0.3854 |
| Thallium(I) acetate | 0.3751 |
| Sodium phosphate monobasic monohydrate | 0.3418 |
| Sodium bicarbonate | 0.3242 |
| Sodium nitrite | 0.3023 |
| Sodium selenite pentahydrate | 0.2998 |
| Cadmium chloride hemipentahydrate | 0.2809 |
| Ferric chloride | 0.2642 |
| sodium iodide | 0.2617 |
| Barium chloride dihydrate | 0.1756 |
| Calcium chloride dihydrate | 0.1455 |
| copper (II) chloride dihydrate | 0.1069 |
| Potassium tellurite hydrate | 0.1044 |
| Zinc chloride | 0.1037 |
| Europium(III) chloride | 0.1036 |
| Aluminum chloride hydrate | 0.0961 |
| Cerium(III) chloride | 0.0189 |
| Lead(II)chloride | 0.0174 |
| Sodium hypochlorite | 0.0048 |
| Manganese (II) chloride tetrahydrate | 0.0037 |
| Sodium deoxycholate monohydrate | 0.0027 |
| Chromium(III) Chloride Hexahydrate | 0.0003 |

The higher C:N ratios do not always favor NH$_4^+$ production. In general, fermentable carbon sources favor NH$_4^+$ production. In general, higher NO$_2^-$ disfavors NH$_4^+$ production. In organic compounds can greatly influence the capacity for nitrate reduction and can alter end-products.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising: (a) L-Sorbose and optionally one or more of the following carbon compounds: D-Serine, L-Arginine, Trisodium citrate dehydrate, L-Arabinose, L-Methionine, Citric Acid, Cytidine, L-Citrulline, L-Alanine, Carnitine Hydrochloride, Inosine, L-Malic acid disodium salt monohydrate, D-Fructose, D,L-Malic Acid, L-Phenylalanine, Itaconic Acid, Glucuronamide, Cytosine, D-Ribose, Sodium L-Lactate, L-Threonine, D-Salicin, D-Glucose, 4-Hydroxybenzoic Acid, L-Glutamine, a-Ketoglutaric acid disodium salt hydrate, m-Inositol, Adenosine, L-Aspartic Acid, L-Tryptophan, Sodium octanoate, D-Arabinose, Putrescine Dihydrochloride, L-Serine, Glycerol, D-Gluconic Acid sodium salt, Gly-DL-Asp, L-Asparagine, D-Glucosamine Hydrochloride, Sodium D-Lactate, D-Tagatose, D-Cellobiose, L-Isoleucine, Xylitol, Potassium oxalate monohydrate, Thymine, Gly-Glu, Parabanic Acid, 5-Keto-D-Gluconic Acid potassium salt, L-Histidine, L-Rhamnose monohydrate, D-Alanine, Sucrose, N-Acetyl-D-Glucosamine, a-Cyclodextrin, L-Leucine, L-Fucose, D-Xylose, Thymidine, Sodium butyrate, Sodium succinate dibasic hexahydrate, D-Raffinose pentahydrate, D-Glucuronic Acid, L-Lysine, and Glycolic Acid, and (b) Sodium bromate, Nickel (II) chloride hexahydrate, Ethylenediamine-N,N'-disuccinic acid, or Cesium chloride, and optionally one or more of the following inorganic compounds: Sodium bromate, Nickel (II) chloride hexahydrate, Ethylenediam ine-N,N'-disuccinic acid, Cesium chloride, Cobalt chloride hexahydrate, Sodium Chloride, sodium iodate, Sodium metavanadate, Sodium 2-mercaptoethanesulfonate, Sodium selenite, Sodium hypophosphite monohydrate, Hans 100x vitamins, Sodium periodate, Magnesium chloride hexahydrate, Sodium molybdate, 9,10-Anthraquinone-2,7-disulphonic acid (AQDS), Sodium cholate hydrate, Potassium chromate, Sodium 2-bromoethanesulfonate, Sodium perchlorate monohydrate, Gallic Acid, Sodium m-arsenite, Sodium nitrate, Lithium chloride, Strontium chloride, Sodium arsenate dibasic heptahydrate, Bile salts, Sodium silicate, sodium sulfite, Sodium antimonite, Gjerstad humics, Ammonium sulfite monohydrate, Vanillyl Alcohol, dimethyl sulfone, silver sulfate, Sodium Chlorate, Sodium tungstate dehydrate, potassium tellurate, sodium fluoride, rubidium chloride, 4-Hydroxyacetophenone, Sodium phosphite dibasic pentahydrate, Sodium Chlorite, Sodium Fluorophosphate, Ammonium chloride, and Gallium (III) chloride; wherein the composition lacks one or more of the carbon compounds listed in Table 1 which have a corresponding ammonium/OD ratio of equal to 1.00 or less, and lacks one or more of the inorganic compounds listed in Table 2 which have a corresponding NH$_4$+IC$_{50}$/growth IC$_{50}$ ratio of equal to 1.00 or less.

2. The composition of claim 1, wherein the composition comprises: (a) five or more of the following carbon compounds: D-Serine, L-Arginine, Trisodium citrate dehydrate, L-Arabinose, L-Methionine, Citric Acid, Cytidine, L-Citrulline, L-Alanine, Carnitine Hydrochloride, Inosine, L-Malic acid disodium salt monohydrate, D-Fructose, D,L-Malic Acid, L-Phenylalanine, Itaconic Acid, Glucuronamide, Cytosine, D-Ribose, Sodium L-Lactate, L-Threonine, D-Salicin, D-Glucose, 4-Hydroxybenzoic Acid, L-Glutamine, a-Ketoglutaric acid disodium salt hydrate, m-Inositol, Adenosine, L-Aspartic Acid, L-Tryptophan, Sodium octanoate, D-Arabinose, Putrescine Dihydrochloride, L-Serine, Glycerol, D-Gluconic Acid sodium salt, Gly-DL-Asp, L-Asparagine, D-Glucosamine Hydrochloride, Sodium D-Lactate, D-Tagatose, D-Cellobiose, L-Isoleucine, Xylitol, Potassium oxalate monohydrate, Thymine, Gly-Glu, Parabanic Acid, 5-Keto-D-Gluconic Acid potassium salt, L-Histidine, L-Rhamnose monohydrate, D-Alanine, Sucrose, N-Acetyl-D-Glucosamine, a-Cyclodextrin, L-Leucine, L-Fucose, D-Xylose, Thymidine, Sodium butyrate, Sodium succinate dibasic hexahydrate, D-Raffinose pentahydrate, D-Glucuronic Acid, L-Lysine, and Glycolic Acid, and (b) five or more of the following inorganic compounds: Sodium bromate, Nickel (II) chloride hexahydrate, Ethylenediam ine-N,N'-disuccinic acid, Cesium chloride, Cobalt chloride hexahydrate, Sodium Chloride, sodium iodate, Sodium metavanadate, Sodium 2-mercaptoethanesulfonate, Sodium selenite, Sodium hypophosphite monohydrate, Hans 100 x vitamins, Sodium periodate, Magnesium chloride hexahydrate, Sodium molybdate, 9,10-Anthraquinone-2,7-disulphonic acid (AQDS), Sodium cholate hydrate, Potassium chromate, Sodium 2-bromoethanesulfonate, Sodium perchlorate monohydrate, Gallic Acid, Sodium m-arsenite, Sodium nitrate, Lithium chloride, Strontium chloride, Sodium arsenate dibasic heptahydrate, Bile salts, Sodium silicate, sodium sulfite, Sodium antimonite, Gjerstad humics, Ammonium sulfite monohydrate, Vanillyl Alcohol, dimethyl sulfone, silver sulfate, Sodium Chlorate, Sodium tungstate dehydrate, potassium tellurate, sodium fluoride, rubidium chloride, 4-Hydroxyacetophenone, Sodium phosphite dibasic pentahydrate, Sodium Chlorite, Sodium Fluorophosphate, Ammonium chloride, and Gallium (III) chloride.

3. The composition of claim 2, wherein the composition comprises: (a) ten or more of the following carbon compounds: D-Serine, L-Arginine, Trisodium citrate dehydrate, L-Arabinose, L-Methionine, Citric Acid, Cytidine, L-Citrulline, L-Alanine, Carnitine Hydrochloride, Inosine, L-Malic acid disodium salt monohydrate, D-Fructose, D,L-Malic Acid, L-Phenylalanine, Itaconic Acid, Glucuronamide, Cytosine, D-Ribose, Sodium L-Lactate, L-Threonine, D-Salicin, D-Glucose, 4-Hydroxybenzoic Acid, L-Glutamine, a-Ketoglutaric acid disodium salt hydrate, m-Inositol, Adenosine, L-Aspartic Acid, L-Tryptophan, Sodium octanoate, D-Arabinose, Putrescine Dihydrochloride, L-Serine, Glycerol, D-Gluconic Acid sodium salt, Gly-DL-Asp, L-Asparagine, D-Glucosamine Hydrochloride, Sodium D-Lactate, D-Tagatose, D-Cellobiose, L-Isoleucine, Xylitol, Potassium oxalate monohydrate, Thymine, Gly-Glu, Parabanic Acid, 5-Keto-D-Gluconic Acid potassium salt, L-Histidine, L-Rhamnose monohydrate, D-Alanine, Sucrose, N-Acetyl-D-Glucosamine, a-Cyclodextrin, L-Leucine, L-Fucose, D-Xylose, Thymidine, Sodium butyrate, Sodium succinate dibasic hexahydrate, D-Raffinose pentahydrate, D-Glucuronic Acid, L-Lysine, and Glycolic Acid, and (b) ten or more of the following inorganic compounds: Sodium bromate, Nickel (II) chloride hexahydrate, Ethylenediam ine-N,N'-disuccinic acid, Cesium chloride, Cobalt chloride hexahydrate, Sodium Chloride, sodium iodate, Sodium metavanadate, Sodium 2-mercaptoethanesulfonate, Sodium selenite, Sodium hypophosphite monohydrate, Hans 100x vitamins, Sodium periodate, Magnesium chloride hexahydrate, Sodium molybdate, 9,10-Anthraquinone-2,7-disulphonic acid (AQDS), Sodium cholate hydrate, Potassium chromate, Sodium 2-bromoethanesulfonate, Sodium perchlorate monohydrate, Gallic Acid, Sodium m-arsenite, Sodium nitrate, Lithium chloride, Strontium chloride, Sodium arsenate dibasic heptahydrate, Bile salts, Sodium silicate, sodium sulfite, Sodium antimonite, Gjerstad humics, Ammonium sulfite monohydrate, Vanillyl Alcohol, dimethyl sulfone, silver sulfate, Sodium Chlorate, Sodium tungstate dehydrate, potassium tellurate, sodium fluoride, rubidium chloride, 4-Hydroxyacetophenone, Sodium phosphite dibasic pentahydrate, Sodium Chlorite, Sodium Fluorophosphate, Ammonium chloride, and Gallium (III) chloride.

4. The composition of claim 1, wherein the first composition comprises L-Sorbose, D-Serine, L-Arginine, Trisodium citrate dehydrate, and L-Arabinose, Sodium bromate, Nickel (II) chloride hexahydrate, Ethylenediamine-N,N'-disuccinic acid, Cesium chloride, and Cobalt chloride hexahydrate.

5. A method of enhancing microbial conversion of nitrate into ammonium comprising: administering to a soil or substrate the composition of claim 1.

6. The method of claim 5, wherein the soil or substrate has a plant or plants planted, or a seed or seeds sowed, in the soil or substrate.

7. The method of claim 5, further comprising introducing of a fertilizer and/or nitrate to the soil or substrate.

* * * * *